(12) United States Patent
Sachs

(10) Patent No.: US 7,427,292 B2
(45) Date of Patent: Sep. 23, 2008

(54) MAXIMAL NASAL INTERNAL SUPPORT SYSTEM

(76) Inventor: Michael Sachs, 128 Central Park South, New York, NY (US) 10019

( * ) Notice: Subject to any disclaimer, the term of this patent is extended or adjusted under 35 U.S.C. 154(b) by 0 days.

(21) Appl. No.: 09/855,942

(22) Filed: May 16, 2001

(65) Prior Publication Data
US 2002/0173848 A1    Nov. 21, 2002

(51) Int. Cl.
*A61F 2/18* (2006.01)
*A61F 2/30* (2006.01)

(52) U.S. Cl. .......................... 623/10; 606/60
(58) Field of Classification Search ............... 606/60, 606/61, 69, 70, 71; 623/10
See application file for complete search history.

(56) References Cited

U.S. PATENT DOCUMENTS

| | | | | |
|---|---|---|---|---|
| 4,597,764 A * | 7/1986 | Black | | 623/10 |
| 4,731,082 A | 3/1988 | Giunta | | 623/10 |
| 4,790,849 A | 12/1988 | Terino | | 623/11 |
| 4,834,096 A | 5/1989 | Oh et al. | | 128/325 |
| 4,938,234 A | 7/1990 | Capriotti | | 128/898 |
| 5,061,280 A * | 10/1991 | Prescott | | 623/10 |
| 5,112,353 A | 5/1992 | Johansson et al. | | 623/10 |
| 5,246,455 A * | 9/1993 | Shikani | | 623/10 |
| 5,423,858 A * | 6/1995 | Bolanos et al. | | 606/220 |
| 5,554,194 A | 9/1996 | Sanders | | 623/16 |
| 5,669,377 A | 9/1997 | Fenn | | 128/200.24 |
| 5,716,405 A | 2/1998 | Mittelman | | 623/10 |
| 5,728,157 A * | 3/1998 | Prescott | | 424/423 |
| 5,800,550 A * | 9/1998 | Sertich | | 623/17.16 |
| 5,871,543 A | 2/1999 | Hoffmann | | 623/20 |
| 5,951,601 A * | 9/1999 | Lesinski et al. | | 623/10 |
| 6,325,755 B1 * | 12/2001 | Bushek et al. | | 600/25 |
| 6,350,265 B1 * | 2/2002 | Blaustein et al. | | 606/71 |
| 6,358,281 B1 * | 3/2002 | Berrang et al. | | 623/10 |
| 6,520,964 B2 * | 2/2003 | Tallarida et al. | | 606/71 |
| 6,547,790 B2 * | 4/2003 | Harkey, III et al. | | 606/61 |
| 6,599,320 B1 | 7/2003 | Kuslisch et al. | | 623/17.11 |
| 6,613,053 B1 | 9/2003 | Collins et al. | | 606/69 |
| 6,746,396 B1 | 6/2004 | Segermark et al. | | 600/233 |

OTHER PUBLICATIONS

Synthes Maxillofacial, Sep. 1997, pp. 1-7 to 1-17; 1-29 to 1-41; 1-47 -1-51; 2-17 to 2-37.

* cited by examiner

*Primary Examiner*—Fenn C Mathew
(74) *Attorney, Agent, or Firm*—Fitzpatrick, Cella, Harper & Scinto

(57) ABSTRACT

The present invention provides a number of novel implants for use in cosmetic and reconstructive nasal surgery, and kits and structural elements comprising various combinations of those implants. The invention includes a technique for securing various implants to each other that will reduce the complexity of the surgery and the required operating time. Another aspect of the invention includes structures that permit the quick and yet secure attachment to each other of various elements, in a way that the surgeon can use to build up a desired shape and provide actual structural support for the involved portion of the patient's features.

11 Claims, 14 Drawing Sheets

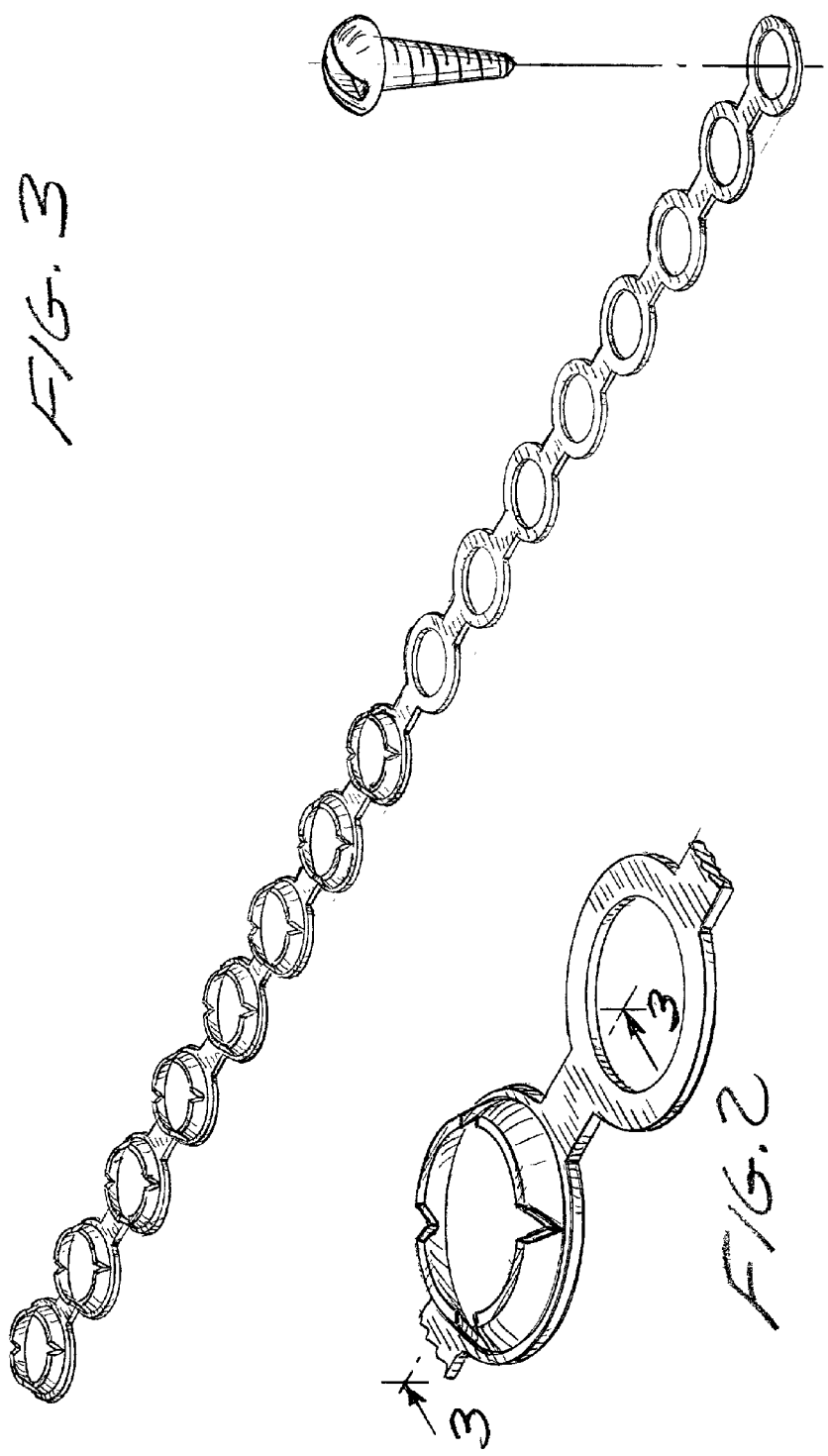

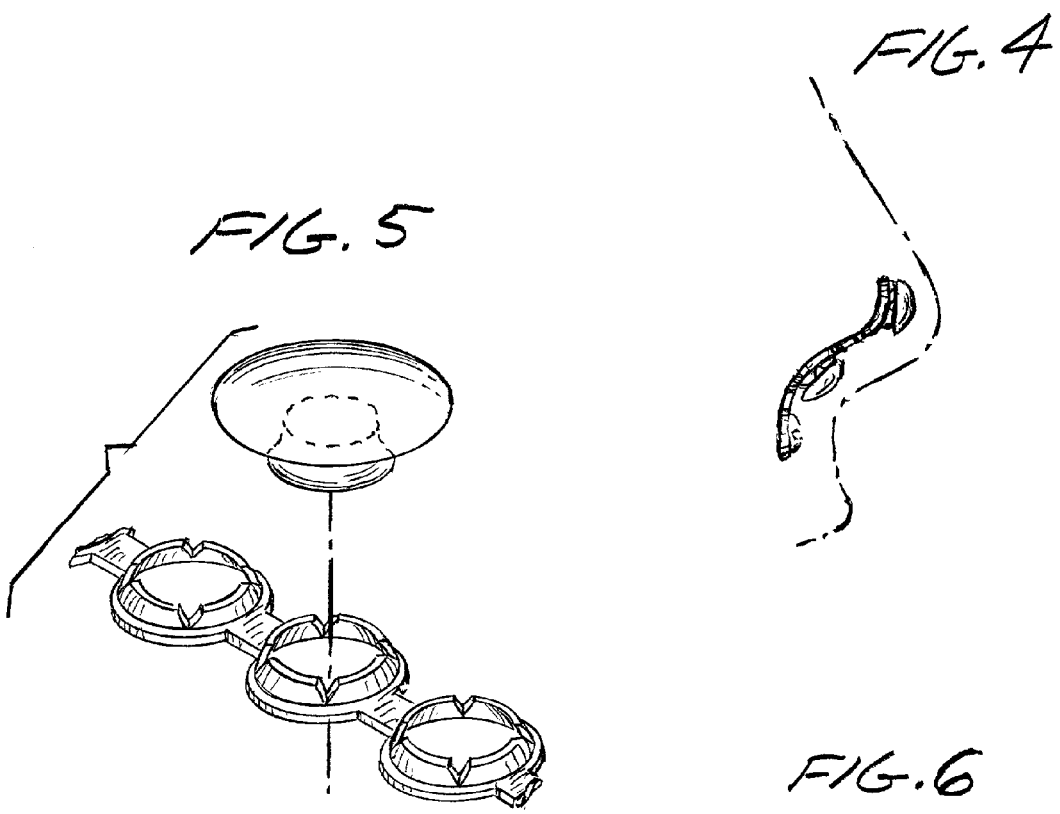
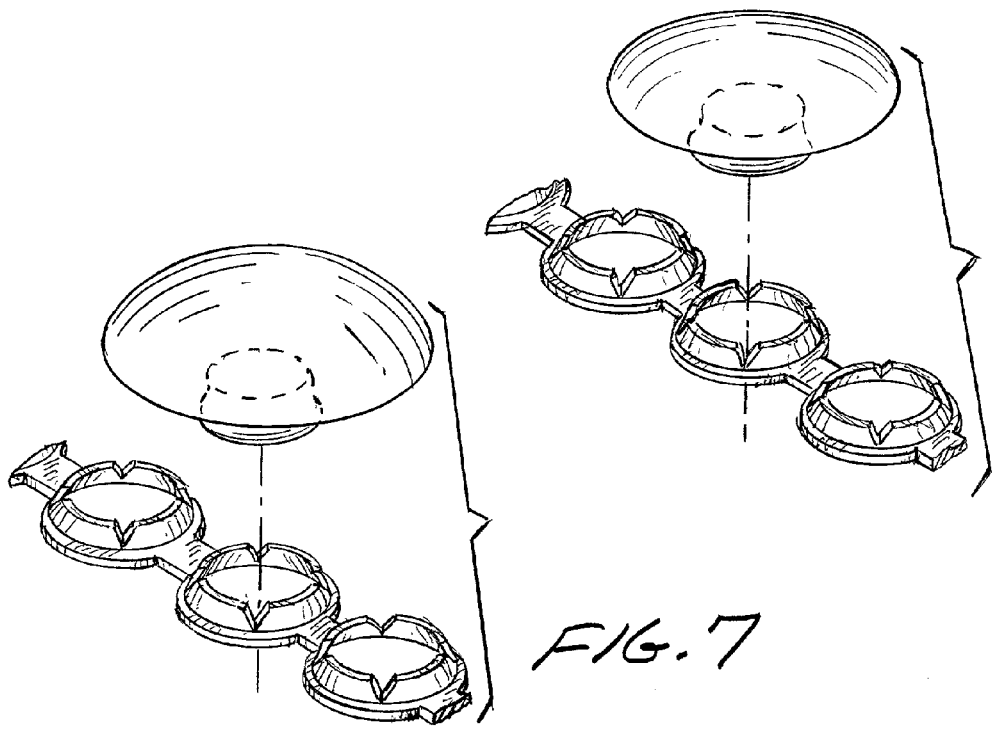

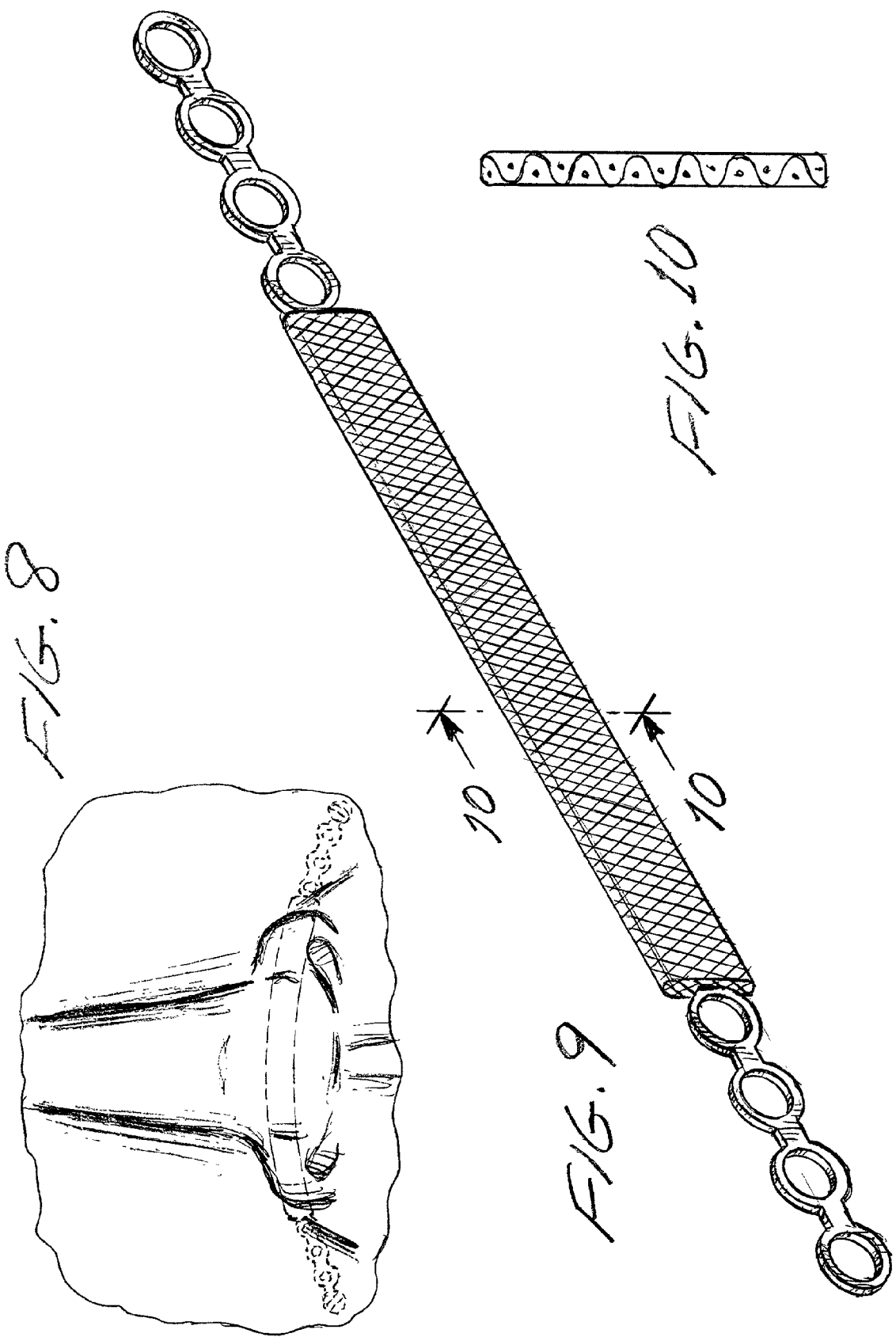

FIG. 15
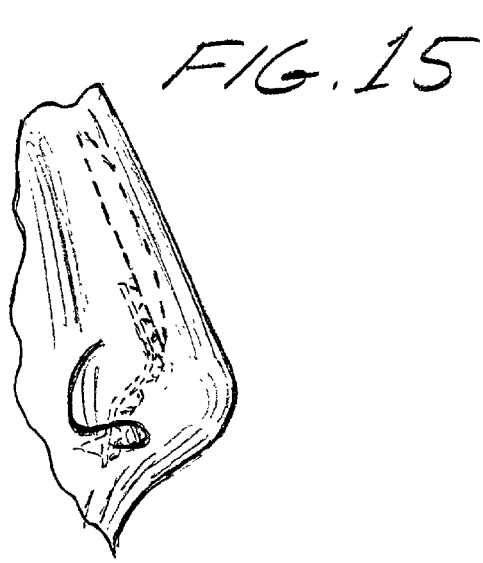
FIG. 16
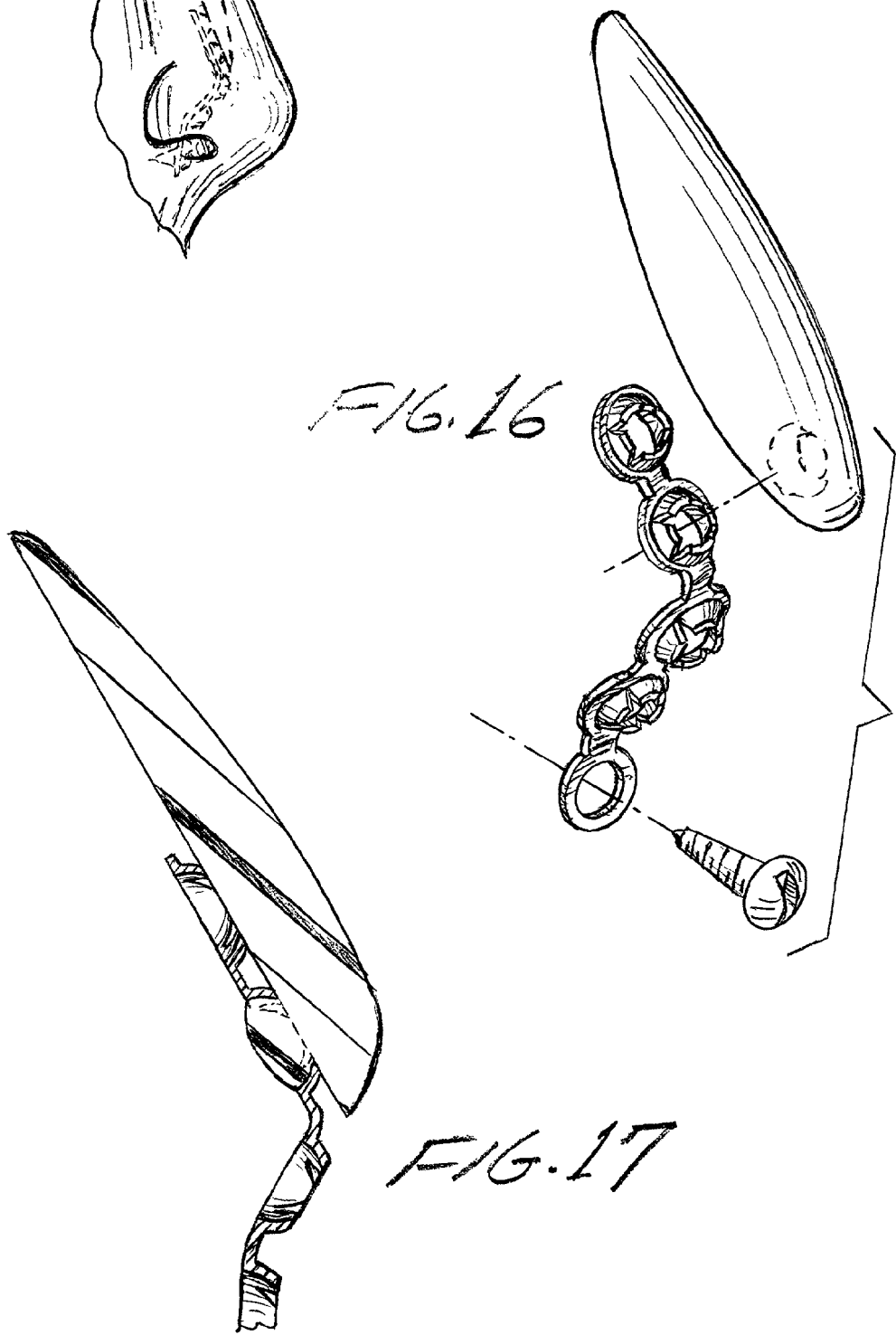
FIG. 17

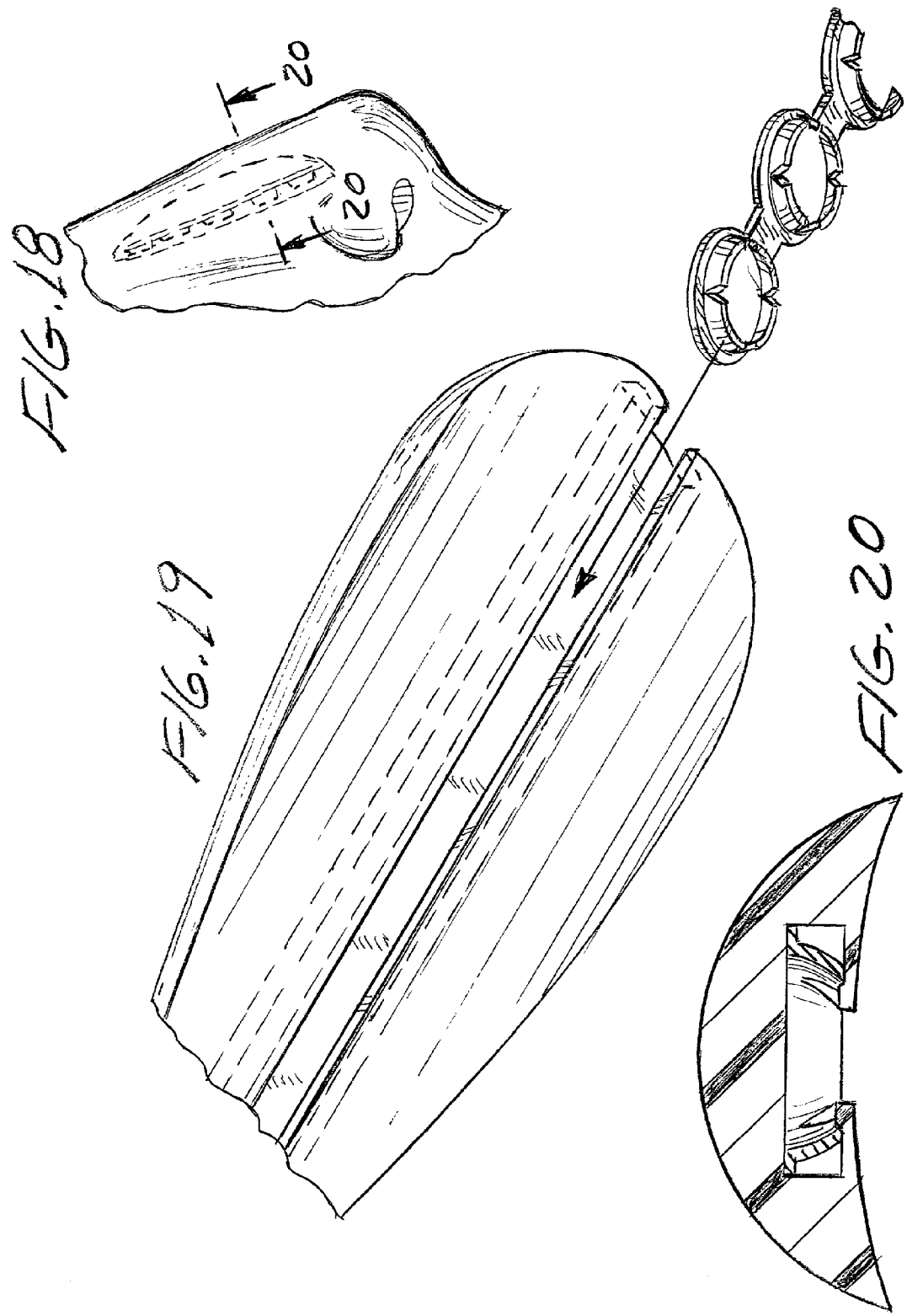

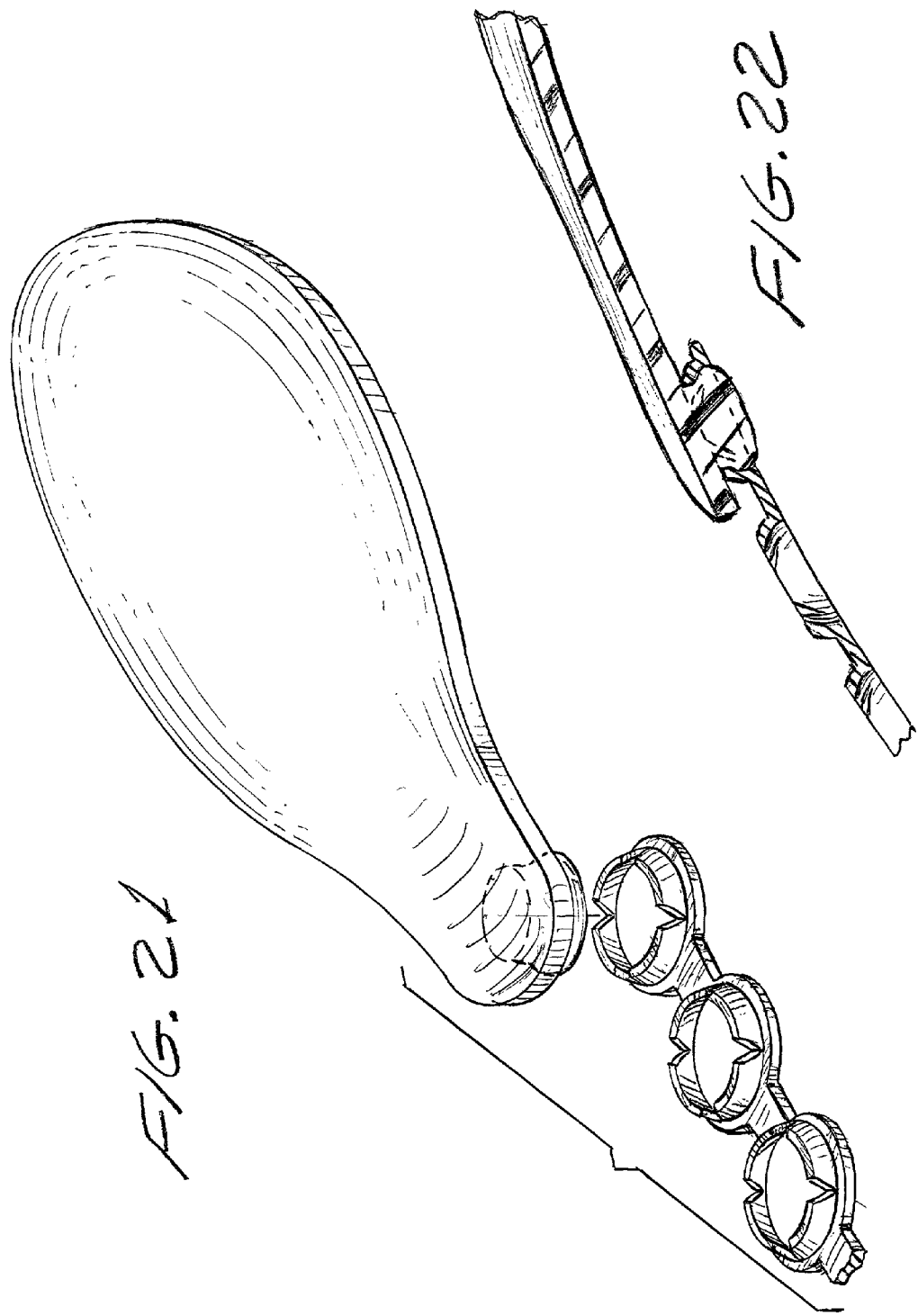

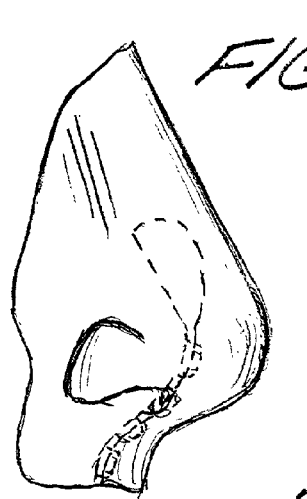
FIG.30
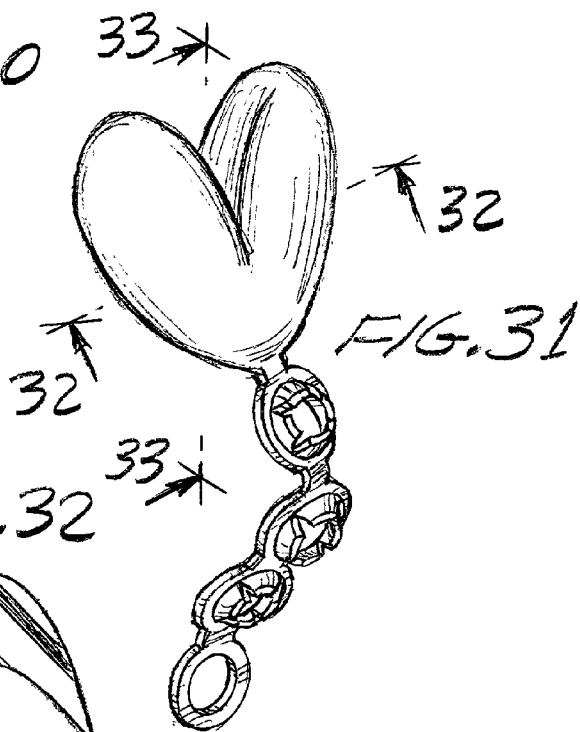
FIG.31
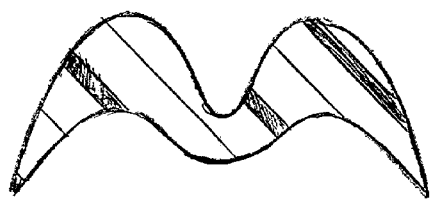
FIG.32
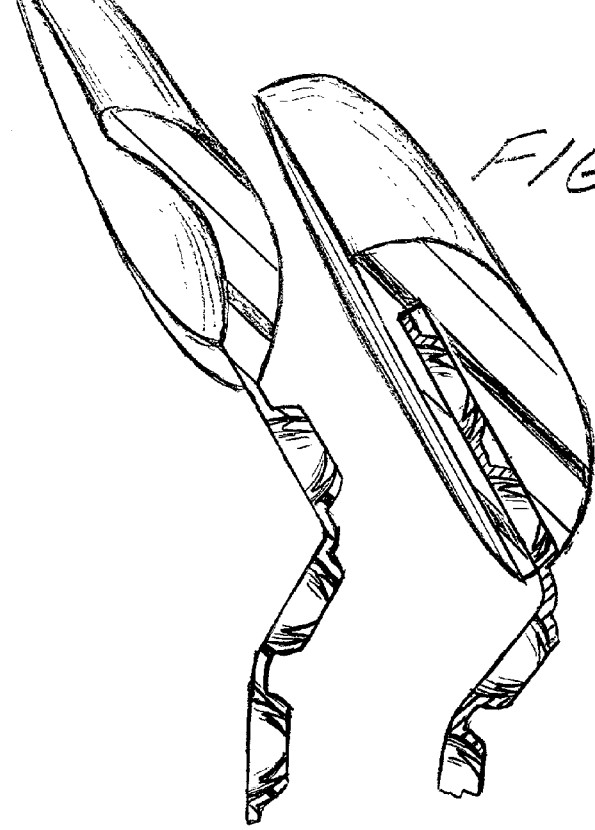
FIG.33
FIG.35
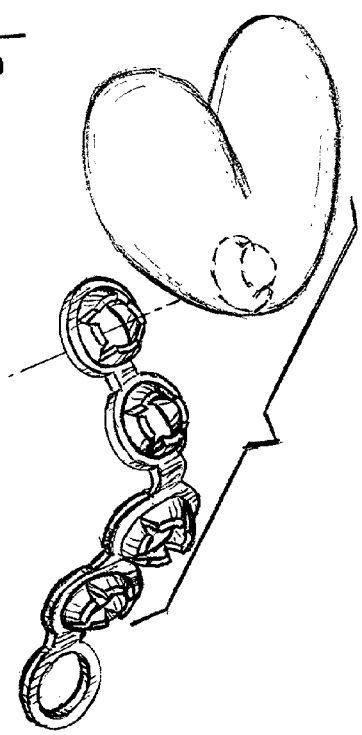
FIG.34

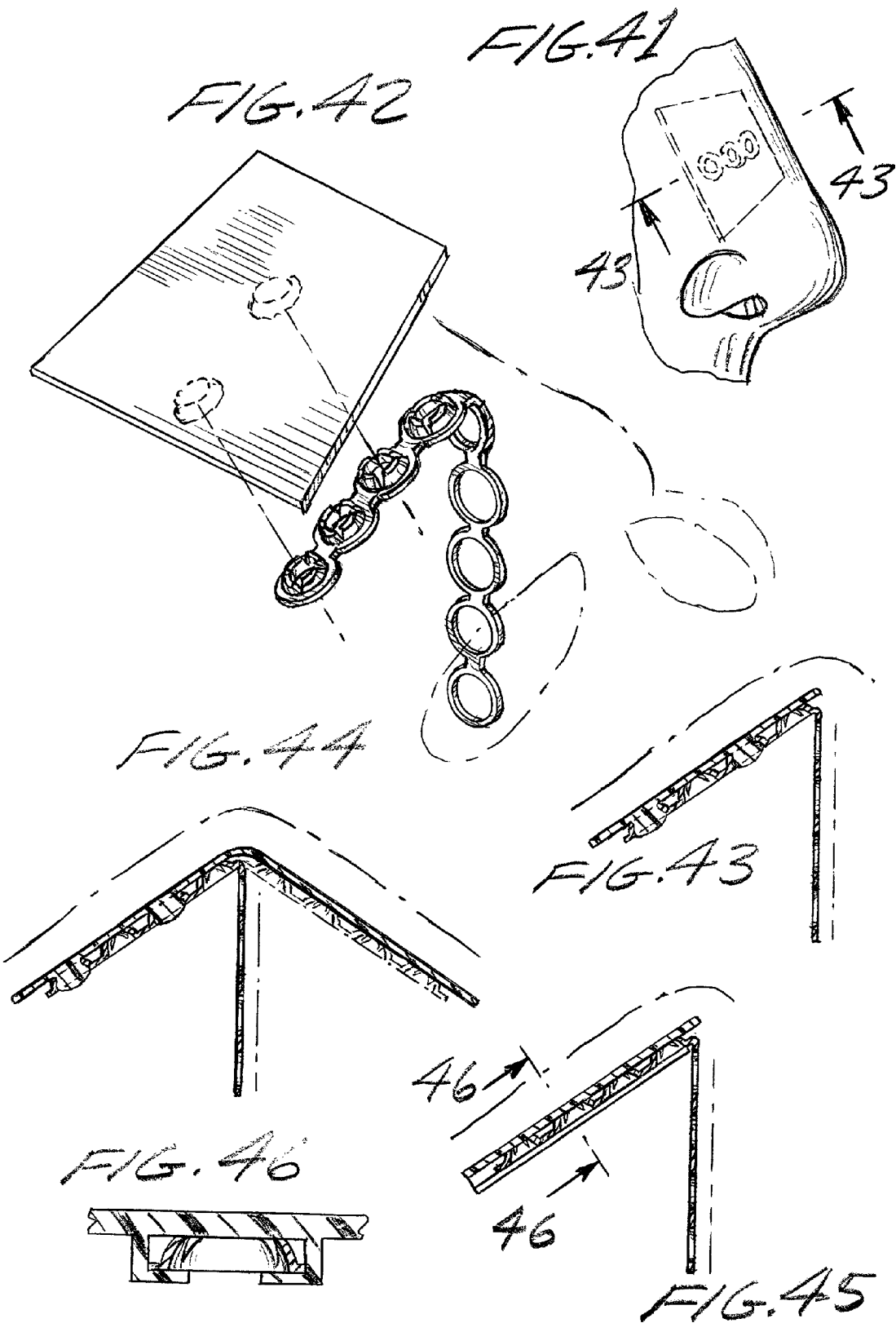

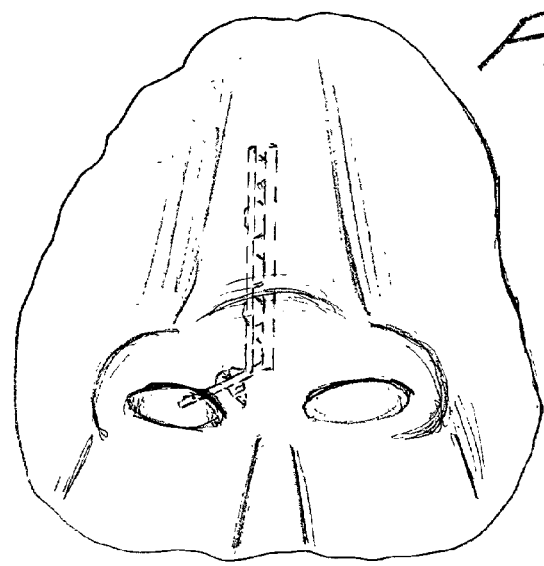
FIG.47
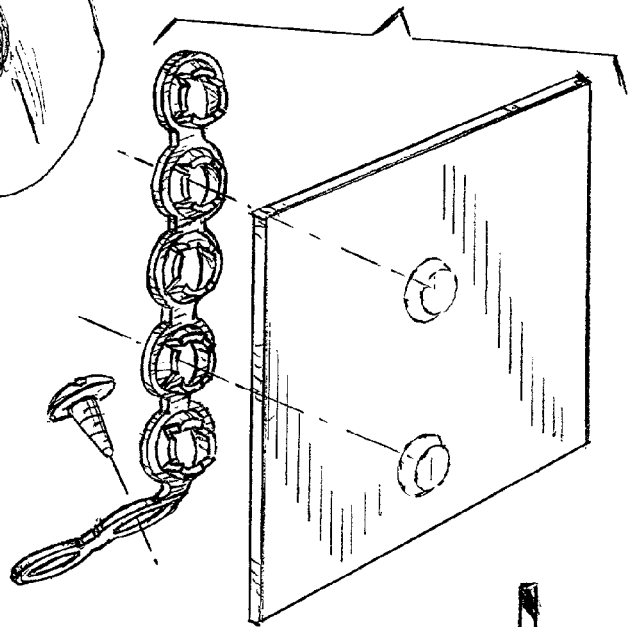
FIG.48
FIG.49
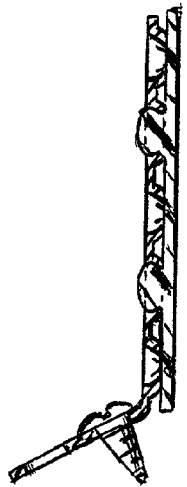
FIG.51
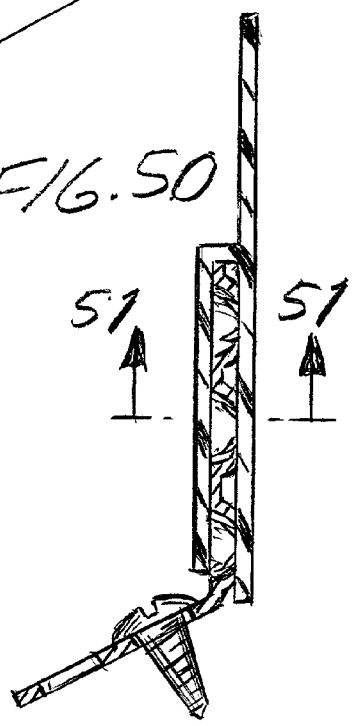
FIG.50

MAXIMAL NASAL INTERNAL SUPPORT SYSTEM

BACKGROUND OF THE INVENTION

1. Field of the Invention

The present invention relates generally to the field of surgical kits, and relates more particularly to such kits for use in performing procedures for cosmetic and reconstructive nasal surgery.

2. Related Background Art

Surgical kits as such are well known. In addition, implants of various kinds are commercially available for use in cosmetic surgery. Examples are titanium implants in various shapes, including straight bars, Y-shaped bars, and T-shaped and L-shaped bars of various dimensions. These implants which are referred to above as "bars" are actually formed as a series of planar rings or annuli joined by short straight pieces that are co-planar with the annuli. In addition, metal plates of various shapes are commercially available. At present, sources of such implants include KLS, Leibinger and Synthes.

In conventional practice, such implants are fixed in placed by such measures as screws, which secure the implants to the patient's bone. These techniques are well known in the art.

It would be advantageous to have such implants that can easily and reliably be secured to each other. It would also be desirable to facilitate the surgeon's task by providing kits of pre-assembled combinations of augments with the structures that will secure them in place. In addition, the possibilities for creative new techniques in cosmetic surgery are far from being exhausted by the present conventional techniques and procedures.

SUMMARY OF THE INVENTION

The present inventor has designed a number of novel implants for use in cosmetic surgery, and kits comprising various combinations of those implants. The invention also includes a novel technique for securing various implants to each other that will reduce the complexity of the surgeon's task and the required operating time. Another aspect of the invention includes structures that permit the quick and yet secure attachment to each other of various elements, in a way that the surgeon can use to build up a desired shape and provide actual structural support for the involved portion of the patient's features.

These implants have characteristics that make them particularly advantageous for use in certain surgical procedures. Some or all of these procedures themselves represent an advance over conventional practice; it should be clearly understood, nonetheless, that the present inventor disclaims the surgical procedures themselves, and seeks only to protect the mentioned kits, implants and structural elements.

According to one aspect of the present invention is provided a surgical implant having a connector element, which connector element is either a female connector element or a male connector element, with the male and female connector elements being respectively shaped such as to be snappingly attachable to each other.

In another aspect, the invention is directed to a surgically-implantable augment that has such a connector element.

In another aspect, the invention is directed to a strut that has at least one such connector element.

In yet another aspect, the invention is directed to a surgical kit, including at least one surgical implant having such a connector element.

In still another aspect, the invention is directed to a surgically-implantable connector system that includes a female connector element and a male connector element, the male and female connector elements being respectively shaped such as to be snappingly attachable to each other.

In yet another aspect, the invention is directed to a surgical implant, for implantation into a patient, comprising an augment module and a strut permanently secured to each other.

BRIEF DESCRIPTION OF THE FIGURES

FIG. 1 is a perspective view of a straight bar, or strut, with holes, according to a preferred embodiment of the present invention.

FIG. 2 is a detail of the strut of FIG. 1.

FIG. 3 is a sectional view of a portion of the strut, taken from line 3-3 in FIG. 2.

FIG. 4 is a schematic view illustrating one example of the placement of the strut like that of FIG. 1 in a rhinoplastic procedure.

FIG. 5 is a view of a button-shaped augment, secured to a strut like that of FIG. 1, showing the manner of connection.

FIGS. 6 and 7 are views similar to FIG. 5, illustrating two variants of the augment (varying in size).

FIG. 8 is a schematic view illustrating the use in rhinoplasty of another implant according to a preferred embodiment of the invention.

FIG. 9 is a perspective view of the implant shown in FIG. 8, having a central titanium mesh portion and end portions for securing the mesh in place.

FIG. 10 is a sectional view from line 10-10 in FIG. 9.

FIGS. 15-17 are views, corresponding to those of FIGS. 11-13, showing a modification of the dorsal augment of FIG. 12, and its use.

FIGS. 18-20 are views illustrating another modification of the dorsal augment of FIG. 12, in which a sliding element is included.

FIG. 21 is a view illustrating a tip, or nose augment, and its manner of connection to a strut like that of FIG. 1.

FIG. 22 is a view, partly in section, showing the tip of FIG. 21 connected to the strut.

FIGS. 30-35 illustrate a double tip, or bilateral tip, attached in various ways to a strut.

FIGS. 41-43 illustrate a unilateral implant for use as an internal nasal valve support system, and the manner of its connection in use to a strut like that of FIG. 1.

FIG. 44 illustrates a similar bilateral implant.

FIGS. 45 and 46 illustrate a modification of the implant of FIG. 42, with an integral strut.

FIGS. 47-51 illustrate an implant for use in septal reconstruction, and various manners in which it can be connected to a strut.

DETAILED DESCRIPTION OF THE PREFERRED EMBODIMENTS

Figure 11:
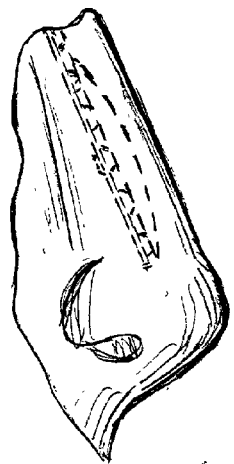
FIG. 11 is a schematic view showing the use in rhinoplasty of a dorsal augment implant according to another preferred embodiment.

As stated above, the devices described and claimed herein were designed for use in rhinoplasty. While the manner of using those devices will be clear to those skilled in cosmetic surgery from a thorough consideration of this disclosure, it may be useful to provide the following brief description of procedures of types to which the present invention is intended to be applied, especially since the devices of the present invention in fact make possible certain cosmetic surgical procedures that have not previously been used. Moreover, for more information on the surgical procedures used in rhinoplasty, reference made be made to various texts on the subject, and in particular to the book *Revision Rhinoplasty: An Exploration of the Craft*, by the present inventor (Springer Verlag, 2001), the entire content of which is incorporated herein by reference.

Titanium is an ideal substance to use for nasal reconstruction. It is inert, strong, and malleable and has many other advantages, which will be outlined below.

One of the most important uses is in nasal reconstruction related to collapse of some or all of the anatomic components which make up the nose, and the preferred embodiments of the present invention utilize titanium as the preferred material in large parts of the implants disclosed herein. (Other materials may be used for certain parts, as set forth below in the detailed descriptions of the implants shown in the figures. Moreover, the description of the preferred embodiments in terms of titanium is not meant to exclude the possible production and use of components and kits using other materials that may be developed, or come into surgical use, subsequently.)

Total nasal collapse is best defined by anatomical region. The upper third of the nose, being derived from bone, can collapse quite easily from too traumatic or complete an osteotomy. When this occurs, the bone is shattered and significantly displaced because the periosteum is disrupted from its attachments to the maxilla. This causes a subluxation of the nasal bones inwardly into the nasal vault. This in turn results not only in significant airway compromise, but gross contour deformities of the upper bony nasal vault. These deformities are extremely difficult to reconstruct.

Middle nasal vault collapse occurs when the upper lateral cartilages are disarticulated from their attachments to the nasal bones. When the nasal bones collapse they often bring with them the upper lateral cartilages, compounding the deformity because the collapse now continues into the middle vault.

Lower one third nasal collapse occurs when the internal and external nasal valves on one or both sides is deficient and the soft tissue of the alar and tip area collapse into the nasal vault. Total collapse occurs when the entire side collapses into each other. Any one of the above situations can occur alone or in combination with one another.

Unilateral upper one third of the nose collapse occurs secondary to subluxation of the nasal bones into the upper nasal vault. This usually occurs during osteotomy if the periosteal lining is ripped away from its lateral attachments with the maxilla.

Reconstruction of this deformity is accomplished with the aid of the light but very strong customized titanium implant. (Throughout this disclosure, the terms "customized", "designed" and "fashioned" refer to the surgeon selecting an appropriate size and shape of implant, and manipulating it as necessary.) The size of the defect is measured and an appropriately sized titanium implant is designed. A medial lip is folded onto the opposite nasal bone and the lateral side of the implant is accurately measured so as to rest on the maxillary ridge of the face. The implant can be placed thorough an inter-cartilaginous incision or alternatively through a low rim type incision over the tip cartilages.

Once the implant is in place, it is stabilized with a holding clamp while external stab incisions are made over the intended screw fastening points. The least amount of screws necessary for stabilization is used. The first screw is placed most superiorly into the frontal bone if possible. If this secures the implant then no additional screws should be used. If an additional screw is deemed necessary then it should be placed inferior to the first one into the stable opposite nasal bone. The small stab incisions are meticulously closed with 6-0 nylon. Generally these incisions heal so well, that they are nearly invisible after one year.

Bilateral bony nasal vault collapse is a much more serious and complicated defect, due mostly to the fact that there does not exist a stable unilateral footing as in the above scenario.

Titanium is again exactingly measured to fit over the nasal bony dorsum. The titanium is designed to extend onto the frontal bones and curved to simulate the nasal dorsum. Lateral extensions are designed to rest on the maxillary bone. These extensions serve two purposes. They add support without the need for direct fastening, and fill in the lateral defect, which occurs when the paired nasal bones both subluxate into the upper nasal vault.

The upper dorsum is exposed via bilateral intercartilaginous incisions. The implant is guided into place through these connected incisions. Two small vertical stab incisions are made over the upper dorsum so that the implant can be fastened into the frontal bones.

If the nasal bone collapse is severe, then due to the anatomic attachments of the upper lateral cartilage to the undersurface of the nasal bone, there can exist a combined collapse, which presents unilaterally. In effect the nasal bone actually pulls the upper lateral cartilage into the mid nasal vault.

In this case, the titanium is fashioned as in the unilateral bony nasal valve collapse except that an extension is designed inferiorly to support the upper lateral cartilage area.

The implant is placed and secured identically as above.

Subtotal upper nasal collapse exists because both nasal bones have collapsed into the nasal vault bringing with them the attached upper lateral cartilages. Since the titanium implant must cover the upper two thirds of the nose, it is quite long. There is not enough strength in the frontal bone area to support the titanium implant from superiorly alone; therefore additional titanium support is required.

The first implant is fashioned from a titanium strip, and will eventually be contoured, intra-nasally to the proper shape. This strip is designed to attach superiorly to the frontal bone and also inferiorly to the maxilla in the area of the nasal spine. This designated "midline strut" will allow for stability and support of the midline, from which the lateral titanium supports can be attached.

The lateral titanium support plate is fashioned from a larger plate to fill in the defect caused by the collapsed nasal bones and their associated upper lateral cartilages. The implant is measured exactly to fit the defect. Inferior extensions are provided to support the upper lateral cartilages.

Exposure for this reconstructive effort is secured via a gingival buccal incision connected to routine transfixtion incisions and unroofing of the soft tissue envelope of the nose. The midline strut is then tunneled into the frontal area. Once in proper position it is secured.

The superior screw is placed into the frontal bone via a stab incision. The implant is then shaped into the desired curve to maximize support and another screw is placed inferiorly via the gingival-buccal incision. The excess titanium strip is trimmed with appropriate scissors.

Final measurements are taken and the titanium plate is trimmed to these specifications. Through an inter-cartilaginous incision, the plate is placed over the midline strut into position. Through a dorsal stab incision the titanium plate is re-checked for position. A stainless steel wire is passed through the midline strut and tied around the plate. The dorsal incision is closed with 6-0 nylon.

Since there is a significant amount of hardware being placed in the nose, in particular around the site of the wire attachment, it is recommended to place autogenous fascia or other soft tissue cushioning (heterogeneous "Alloderm") above the titanium to protect the dorsal skin from the underlying hardware.

At the completion of the reconstruction the lateral profile reveals that the sub-total nasal collapse has been repaired.

A compelling and disastrous cosmetic and functional collapse exists when the nasal tip cartilages combined with the upper lateral cartilages lack enough support to keep the soft tissue of the alar combined with the internal nasal valve from collapsing into the vestibule. One can regard this as a combined internal and external nasal valve collapse.

A right-sided collapse of the internal and external nasal valve presents as a narrowing of the nostril due to the soft tissues of the alar collapsing into the vestibule because they lack the cartilaginous support usually derived from the tip and upper lateral cartilages. This support may be lacking due to overzealous resection during primary rhinoplasty alone or in conjunction with significant scarring of the internal nasal valve and or vestibule. When there is significant vestibular stenosis from a lack of internal mucosa, which has been replaced with scar tissue, then the mucosa of this soft tissue should be completed first.

Although a right-sided combined collapse has been mentioned, the deformity can be bilateral, and can be corrected with the same reconstructive technique. Reconstruction of this defect begins with a partial degloving of the lower portion of the nose through a gingival buccal incision.

The dissection continues superiorly to the level of the nasal bones. The distance from the attachment point on the maxillary ridge to the opposite attachment point is measured. The point of attachment should be lateral enough to gain excellent support for the implant and be relatively flat to allow good fixation. Stevens scissors are used to tunnel from the undersurface of the lip up towards the midline just below the tip cartilages. A secondary tunnel from the other side joins the primary tunnel. The tunnel must not be too superficial.

A titanium implant is placed from one side and tunneled into the other side with the aid of a grasping forceps. The nose is then placed into its normal anatomic position and the size and shape of the implant is evaluated in this position. An Asch forceps can be used to shape and bend the titanium to the desired form.

Lateral and medial adjustment of the screws will cause the tip to project more or less. Once these adjustments are finalized a unilateral screw is attached into the maxillary bone and then the opposite side is screwed into place. The gingival buccal incisions are closed and final adjustment is made digitally to the implant.

Late post-operative adjustments are also possible with the aid of topical anesthesia to gain the right proportion of airway opening and nasal projection.

If there is collapse in the area of the tip cartilage, then a small implant is manufactured from titanium mesh. If collapse exists superiorly to the tip in the upper lateral cartilage area, then a larger implant is designed.

This implant is slipped into a rim incision, which is undermined superiorly until the extent of the reconstruction is reached. The rim incision is closed with 6-0 chromic.

Certain of the devices of the present invention are useful in correcting a severe deviation of the nasal septum, especially where the deviation is in the caudal anterior aspect of the quadrangular cartilage.

Inferior mucoperiosteal and superior mucoperichondrial tunnels are created and eventually joined to expose the deviated portion of the quadrangular cartilage. The tunnels on the left are joined and mucosa is reflected. Similarly, tunnels are created and joined on the right side.

The deviated portion of the inferior edge of the septum is excised sharply with a chisel. This cut can incorporate the pre-maxilla and maxillary crest if these are deemed deviated as well.

Quadrangular cartilage is excised just posterior the caudal deflection. A titanium strut is then measured and placed via screws, into the floor of the nose on or near the maxillary crest, and a strut is placed likewise on the other side. A routine quilting stitch, is utilized to approximate the mucosa and septal cartilage together. The bilateral placement of titanium struts secures the reconstruction.

One particularly important part of the present invention is a fastening system by means of which it is possible to secure two implants quickly and yet permanently to each other without the use of screws. Other important features described below include various implants incorporating that fastening system.

FIG. 1 shows a titanium strut which is an example of such an implant. In the particular example illustrated, the strut is basically linear in overall form, and can be viewed as having two portions. The first portion consists of a series of planar annuli of metal connected in a linear array by short, planar segments. The annuli are suitable for the passage of screws, by means of which the strut can be secured to bone.

The second portion of the strut consists of a similar series of circular elements, also in a linear array and also connected to each other (and to the first portion) by short planar segments. The circular elements, however, are not planar but are each shaped to serve as female connector elements, as described below.

These female connector elements in this embodiment, as shown in greater detail in FIGS. 2 and 3, includes four element, which together have a shape that can be thought of as a segment or band of a spherical shell, divided into four equal sections by four notches. It will be noted that the top, or notched side, of the female connector element (referring to the orientation in FIGS. 2 and 3) is narrower than is the lower side.

In this embodiment, these female connector elements serve as one half of the fastening system of the present invention. The other half of the fastening system is a male connector element, as shown in FIGS. 5-7 (among others).

The male connector element used in the illustrated embodiments is referred to herein as a nipple, and has one end attached to an object (a nose tip, in FIGS. 5-7), and the other, larger end extending therefrom the larger end of the nipple is wider than the opening in the top or notched side of the female connector, but is sized to fit within the wider, lower side. In use, the free end of the nipple is simply pushed like a snap through the notched side of the female connector. It will be appreciated that if the two connector elements are properly sized, this snapping together is very fast and easy.

Based on this, FIG. 1 can be shortened, adapted, changed, manufactured so that the snap and/or the plain circular system can be placed in any way, shape or form at any length.

FIG. 2 shows the two different types of the flat part of the strut or the female snapping part of the strut, and FIG. 3 is a more specific cross-cut view of the mechanism. As part of the whole concept there are certain other components of this system which can be attached to the strut.

FIG. 4 shows a titanium strut like that of FIG. 1 in place intra-nasally, meaning inside the nose, with certain components attached to it. In this illustration, the most inferior part of the strut is attached to the maxillary bone with a screw, with an augment in the columellar portion to reconstruct that area, and another in the tip portion of the nose.

FIG. 5 shows one type of augment according to the invention, a button, provided with the male connector element as described above (this is the type of component shown attached to the strut in FIG. 4). The button can be made of various materials, including silastic, rubber or titanium, although almost any material suitable for surgical implants can be used. The nipple, however, is made of titanium.

FIG. 5 shows the button snapping into the strut.

FIG. 6 and FIG. 7 show various sizes of the button, which can advantageously be provided as part of a kit, so that the surgeon has any needed size at hand.

As indicated FIG. 4, this type of implant would be used for tip collapse, for columellar retraction and for columellar collapse, and for basic collapse of the lower one-third of the nose. This would add support and reconstructive bulk to any reconstructive effort being made to address those problems.

FIG. 9 shows a modification of the strut of FIG. 1. In FIG. 9, plain titanium strut (i.e., not having connector elements as described with respect to FIG. 1) on either side of and attached to a mesh which is for use in construction of the lower third of the nose. The mesh can be fine, medium or coarse, and of different and varying strengths. A kit according to the present invention may advantageously provide a selection of such intrinsic mesh struts.

The intrinsic mesh strut is used, as shown in FIG. 8, for reconstruction of either unilateral or bilateral, internal and/or external nasal valve collapse. As described above, this is placed through an incision in the mouth.

FIG. 11 shows the use of the basic strut of FIG. 1 with a dorsal augmentation component, which includes a nipple positioned so that the component will be medially attached to the titanium strut. This augment will be used in cases of collapse of the upper or mid-nasal dorsum, a collapse which makes it necessary to bulk up or add tissue to this area.

Figure 12:
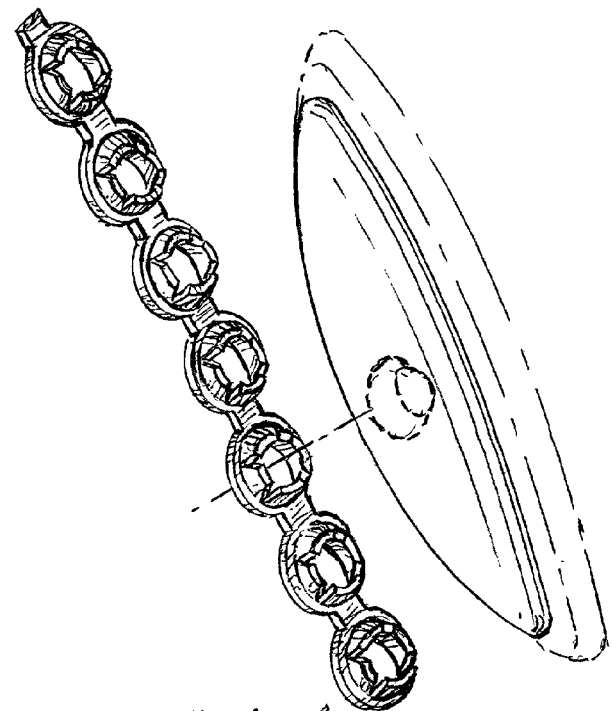
FIG. 12 is an illustration of the insert shown in FIG. 11, and the manner in which it connects to a straight strut like that of FIG. 1.
Figure 13:
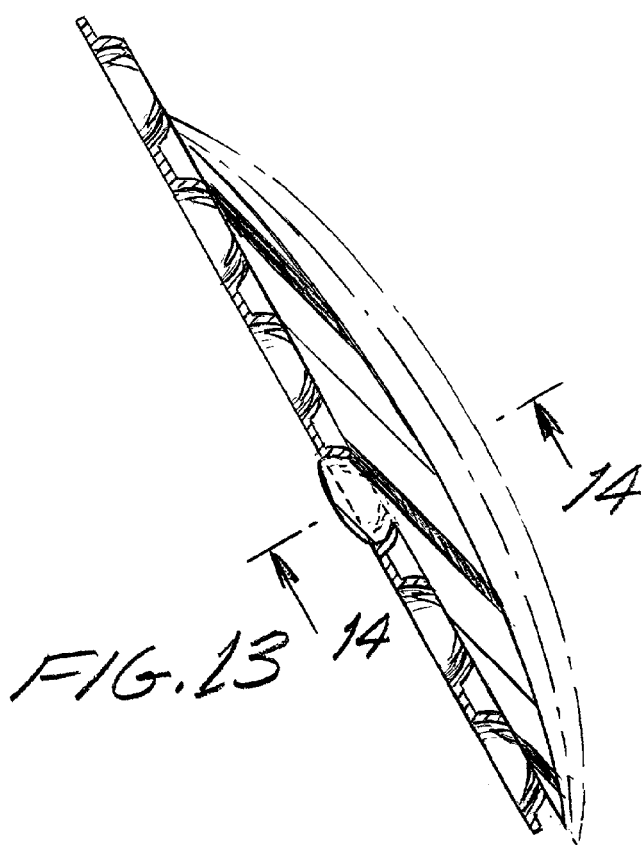
FIG. 13 shows additional detail, partly in section, of the connection illustrated in FIG. 12.
Figure 14:
FIG. 14 is a sectional view taken from line 14-14 in FIG. 13.

The component is shown in FIG. 12 being snapped into the basic titanium strut (FIGS. 13 and 14 show it in place in the strut). The augment itself can be different sizes and different shapes, as indicated by the broken-line outlines in FIGS. 12-14, and various different sizes and shapes are preferably provided in a kit according to the invention, so that the surgeon can select the exact shape suitable according to how high or how much bulk it is desired to add to that part of the nose.

The implantation of this component, again, is performed intra-nasally.

FIG. 15 shows another separate component according to the present invention, a dorsal augmentation component, which unlike that of FIG. 12 has its nipple located so that the augment is inferiorly attached to the strut (see FIGS. 16 and 17). As shown in FIG. 15, the component is actually suspended through one screw in the nasal spine area. Again, various sizes and variations in shape can be provided, the appropriate one being selected by the surgeon based on how badly the tissue is compromised, how much augmentation is necessary, and how much access there is to the nose.

FIG. 18 shows a variation on the dorsal augmentation components described above, in which the augment is attached to the strut of FIG. 1 not by means of a nipple, as in the preceding embodiments, but by part of the length of the strut being slid into a groove provided for that purpose, as shown in detail in FIGS. 19 and 20 (this embodiment may be termed a dorsal augmentation slide-through component). The strut may be slid in at the time of use (which is preferred at present), or can be provided already in place in the augment. This component represents a variation in approach that adds flexibility to the surgeon's reconstructive efforts, by allowing for the augment component to be either intra-nasally slid on to the strut or pre-slid on before it is actually entered into the nose, for more exact placement.

It should be noted that while FIG. 20 shows the augment receiving the end of the strut that has female connector elements, the groove can instead be shaped and sized to receive and snugly engage with the plain end of the basic strut. If it is desired to permit both types of use, the groove may be shaped so that one end of the groove can receive one end of the strut, and the other end of the groove can receive the other end of the strut.

FIG. 21 shows a basic inferiorly attached tip component system, which as shown in FIGS. 21 and 22 is snapped into place with an inferiorly based nipple. This is used for almost any category of tip reconstruction.

Figure 23:
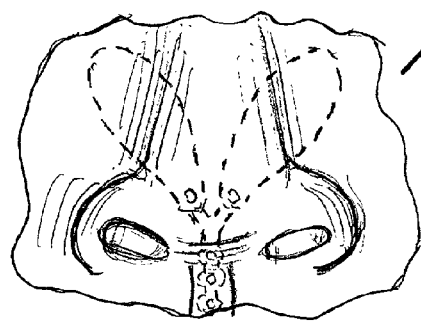
FIGS. 23-28 illustrate the use of one or two such tips with a Y-shaped strut according to another embodiment of the invention.
Figure 24:
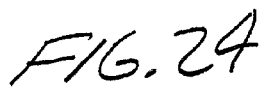
Figure 25:
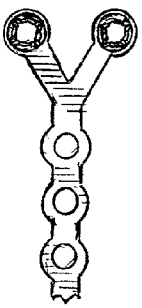

FIG. 23 shows a bilateral variation of the system of FIG. 21 for use if both tips need to be reconstructed. As shown in FIGS. 23 and 24, the tips are actually a part of the strut and do not need to be attached at the time of use. Accordingly, the tips may be pre-attached to the Y-shaped strut by means of the fastening system of the invention, or by other means. FIG. 24 shows the actual strut, and FIG. 25 shows a larger view of it.

Figure 26:
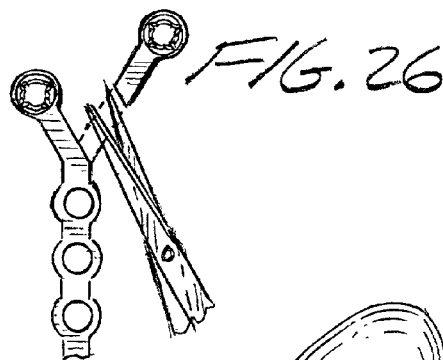
Figure 27:
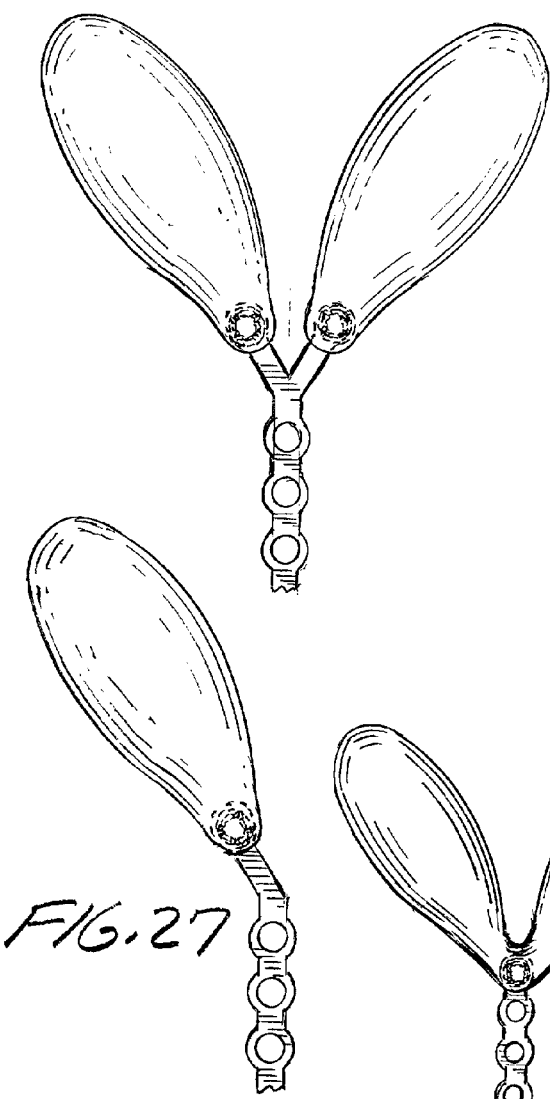
Figure 28:
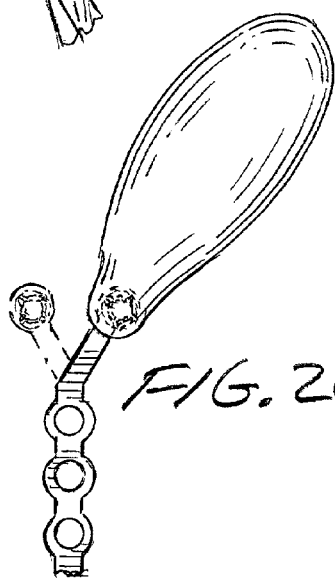

FIG. 26 shows a variation in which one branch of the Y-shaped strut can be cut, permitting this embodiment to be used unilaterally, as in FIG. 27 or FIG. 28 (which show the tip module actually on the strut).

Figure 29:
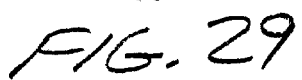
FIG. 29 illustrates a bilateral tip connected to a strut.

FIG. 29 shows another variation of a bilateral tip module in which the two tips of FIG. 23 are replaced with one bilateral tip, which is mounted at the end of a straight strut instead of the Y-shaped strut used in FIG. 23.

FIGS. 30-33 show a separate tip component, in which the tip is a little bulkier, and which accordingly will be termed a heart-shaped tip component. This tip component is attached directly to a strut for placement intra-nasally so there is no necessity for a separate snapping procedure. This may add a little more stability if it is known in fact that the total tip has to be reconstructed.

FIG. 30 shows this component intra-nasally as in use. FIG. 31 shows the actual implant module, and FIGS. 32 and 33 are a cross-section and a side view.

FIG. 34 and 35 show variations. While FIG. 33 shows the actual implant as a one-piece implant, FIG. 35 shows a variation with a slide-through mounting of the augment on the end of a strut according to the invention, and FIG. 34 shows a bilateral heart-shaped tip module that has a nipple and can be snapped onto the strut.

Figure 36:
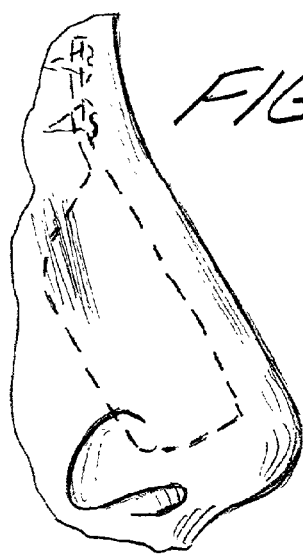
FIGS. 36-38 illustrate a bilateral mesh implant with an integral extension for securing the implant in place.
Figure 37:
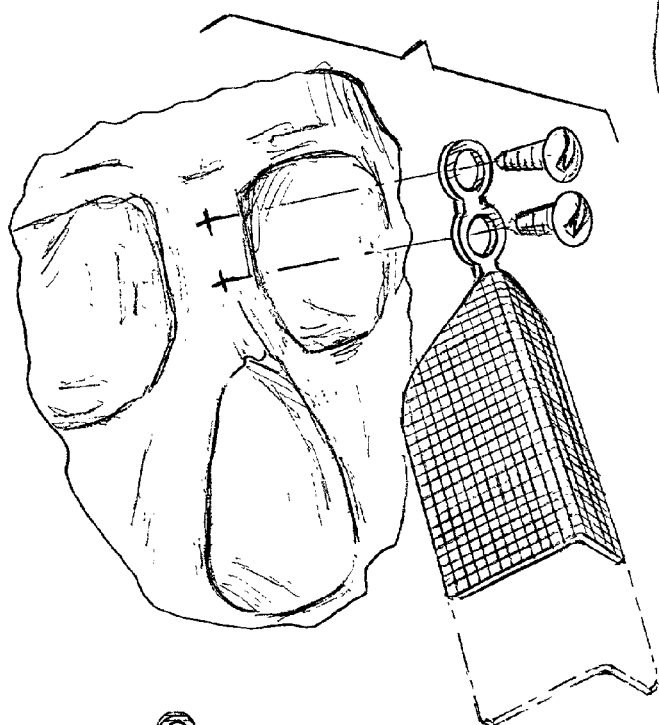
Figure 38:
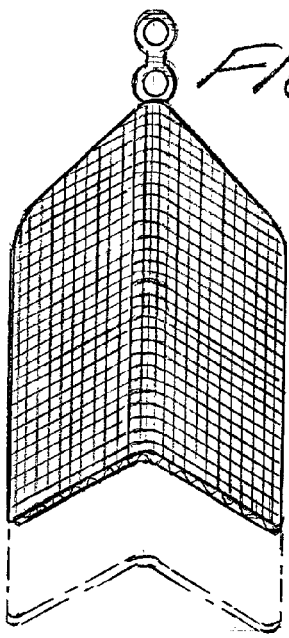
Figure 40:
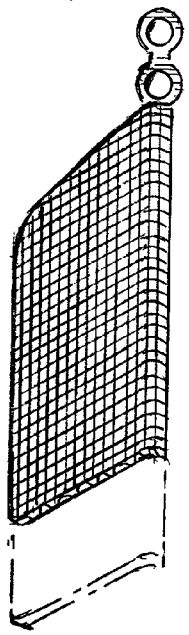
FIGS. 39 and 40 illustrate two unilateral modifications of the implant of FIG. 38.
Figure 39:
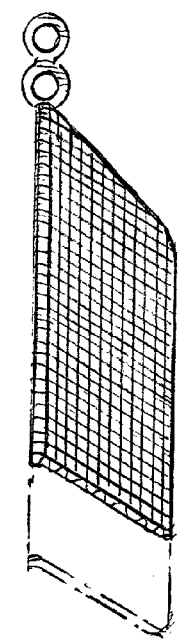

FIGS. 38, 39 and 40 show bilateral and unilateral versions of a bony upper and middle third nasal collapse module. The bilateral version (FIG. 38, and shown also in FIG. 37) is a V-shaped module, in the sense of having a V-shaped cross section due to its having two roughly planar panels of mesh or other suitable material meeting at an angle. The top part is attached intrinsically to a plain strut. The strut is screwed into the upper nasal dorsum or forehead region and acts as a support mechanism for the upper and middle third of the nose either bilaterally as in FIG. 38 or on one or the other side as in FIG. 39 or FIG. 40. FIG. 36 is a view of this system in place.

As with previous embodiments, the broken-line indications show that these components may preferably be provided, in a kit, in various sizes or shapes.

FIGS. 41 and 42 show a middle nasal vault reconstructive module attached with two nipples to the basic strut, using the fastening system of the invention. The basic strut allows this module to be used to reconstruct collapse of the middle nasal vault either unilaterally or bilaterally (see FIG. 41).

FIG. 43 shows how the module looks intra-nasally, and FIG. 44 shows how it looks intra-nasally bilaterally (the broken lines here indicate the nose, albeit only in a general fashion).

FIG. 45 shows a variant in which the module is mounted onto the strut by sliding into place, and FIG. 46 shows a detail of such mounting, in which the module is provided with walls defining a channel on one surface to receive the strut.

FIGS. 47 and 48 illustrate a septal perforation module, which is for use for septal reconstructions. FIG. 47 shows this module intra-nasally, and FIG. 48 shows the septal plate being attached to the basic strut by means of the fastening system of the invention. It is noteworthy that here, as in the embodiment of FIGS. 41 and 42, two nipples are provided on the plate, to ensure proper orientation of the mounted module relative to the strut.

Alternatively, this module can be provided, as shown in FIGS. 50 and 51, with a slide-through mounting arrangement.

Figure 52:
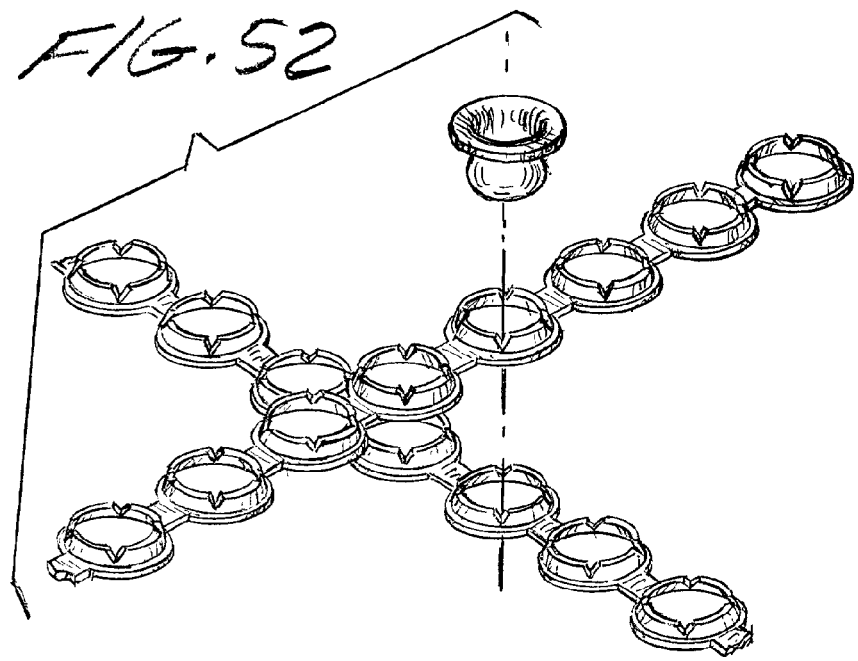
FIGS. 52-54 illustrate a modification of the system of connection shown in the foregoing embodiment, the modification connecting two struts to each other, and using a separate rather than integral male element for effecting the connection.
Figure 53:
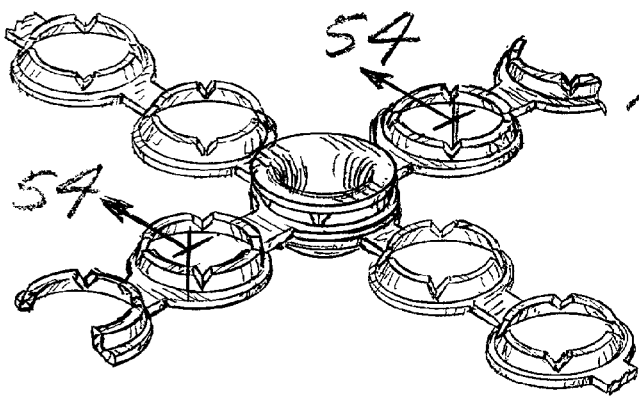
Figure 54:
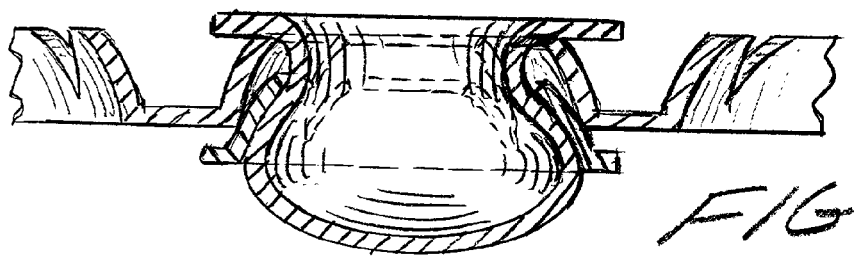

FIG. 52 illustrates another embodiment of the invention, in which two struts are connected together using a version of the fastening system described above. As shown in FIGS. 52-54, a third element, in addition to the two struts themselves, is utilized for this purpose. The third element is a nipple which, unlike those described in the foregoing embodiments, is an independent unit. This nipple is sufficiently long to pass through two of the female connector elements provided on the struts (see FIG. 54).

In addition, the nipple may pass through a plain hole, rather than a female connector element, in the upper strut (this variation is not illustrated). Depending on the shape of the female connector element, this variation may require that the nipple element be shaped somewhat differently. Selecting the appropriate variation in shape of course is within the ordinary skill in the relevant art.

As another variation, which also is not illustrated, such a nipple element may be passed through plain holes in both of the struts, and be snapped into a female connector element which, like the nipple itself, is an independent unit. (It is within the scope of the invention to use such an independent female connector element, or an independent nipple, or both, instead of the arrangements illustrated in the drawings.)

Figure 55:
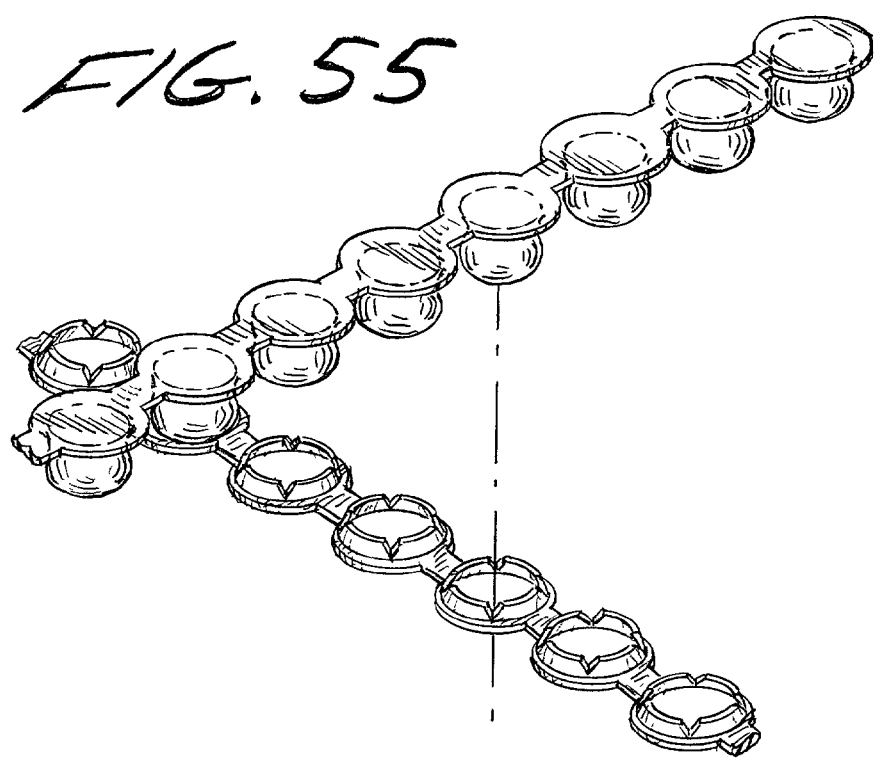
FIGS. 55 and 56 show another manner of connecting two struts according to the invention.
Figure 56:

FIG. 55 shows another variation of two struts overlying each other in a cross-wise direction and attached to each other using a female and a male connector element according to the invention. In this variation, the nipple that serves as the male connector element is provided as a part of one of the struts. This variant can be used as shown in FIG. 56 with a total nasal collapse. In that figure, it is shown with the addition of a dorsal augment system as well as columellar and tip augment systems, as described above, after the two basic struts are attached to the face and the nose, adding additional support and variation.

A number of variations of the foregoing embodiments should be noted as also being within the scope of the invention.

First, any of the augments disclosed as being slid-mountable, may have a groove that is shaped to receive the plain end of a strut, or that is shaped to receive the end having female connector elements, or that is shaped to be able to receive either end of the strut.

Second, any of the slide-mountable augments may be provided with one or more external walls to define a sleeve that is shaped to receive (one or the other) end of the strut.

In addition, multiple nipples, rather than only one, may be provided, wherever one is shown above. Similarly, the number of nipples is not limited to two, but may be any number that is desired.

Also, while a number of preferred and advantageous shapes have been shown for the augment modules, any variation of these shapes, or any other shape, may be used instead, according to what is deemed useful for the particular purpose at hand.

Again, while the struts have all been shown as either straight (linear) or Y-shaped, any other shapes and arrangements are also within the invention, including arrangements in which the connector elements are not all in a linear array (i.e., in which they are arranged in a two-dimensional layout), and/or in which the plain holes (if any) are arranged in a two-dimensional layout.

Moreover, a strut according to the present invention may have either male or female connector elements, or both, and may have any number of each (which need not be the same number), as well as any number of plain holes. Also, the plain holes, female connector elements, and nipples may be in any pattern or sequence, so that for example not all the nipples are together, nor all the female connector elements are together, but both may be interspersed with each other and/or with plain holes.

Also, while the nipples, female connector elements and plain holes in the struts are all shown herein as being circular in shape, other shapes can be used instead or in addition, provided only that the desired security of connection between the male and the female connector elements is obtained. Thus, for example, the female connector element, which is shown herein as having the shape of a segment of a spherical shell, might have a different shape that does not have radial symmetry, provided only that the shape is such as to hold the nipple firmly, while yet providing enough elasticity to permit the nipple to be inserted in the first place.

Moreover, if deemed desirable, it is possible also to provide an augment module that is to be attached to two, or more than two, struts, or that is pre-attached to two or more struts.

Additional variations in the foregoing preferred embodiments are also possible, and are also within the scope of the invention. For example, it is preferred that the connector elements engage each other in a snap fit, and are circular in periphery, as illustrated in FIG. 2, for example; nonetheless, it is within the scope of the invention for the female and male snapping parts to be of other shapes, for example triangular, quadrilateral or otherwise polygonal, provided only that a sufficiently secure engagement is obtained. Moreover, while the illustrated embodiments all have resilience provided in the female snapping portion (into which the complementary nipple portion fits), it is within the scope of the invention to make the female portion solid, that is, without notches, and to split the nipple into individual resilient teeth or detents that fit into and resiliently engage the female portion.

The foregoing description is sufficient to enable one of ordinary skill in the relevant art or arts to make and use the present invention, and to apprise one of ordinary skill of the best mode (if any) contemplated by the inventor of doing so. Nonetheless, many modifications and variations of the foregoing embodiments will be apparent to those skilled in the art, and accordingly, the scope of the invention is not to be limited by the details of the detailed embodiments described herein, but only by the terms of the following claims.

What is claimed is:

1. A rhinoplastic surgical kit comprising at least one implantable strut having a first connector element, and at least one implantable rhinoplastic augment having a second connector element, said rhinoplastic augment having an augmenting surface having a predetermined shape to be imparted to external tissue of the patient from a position at which the augment is implanted within the patient, said first and second connector elements being adapted to engage each other in such manner as to secure themselves together without use of screws, said strut having at least one portion lying in a first plane and extending in a first direction, and said first connector element comprising material extending from said strut in a second direction that is perpendicular to said first direction and to said plane and defining a receptacle exhibiting a degree of resilience and at least a portion of which extends from said plane, and said second connector element comprising material having a shape and size to be received snappingly in such receptacle, and said first and second surgical implants being provided in said kit with said first and said second connector elements not engaging each other.

2. A rhinoplastic surgical kit according to claim 1, wherein said first and second connector elements are shaped to fit together in a mechanical engagement to secure themselves together.

3. A rhinoplastic surgical kit according to claim 2, wherein said first and second connector elements are shaped to fit together snappingly to secure themselves together.

4. A rhinoplastic surgical kit according to claim 3, wherein said first connector element fits inside said second connector element, at least one of said connector elements having sufficient resilience to permit said connector elements to be fitted together into said mechanical engagement to secure themselves together.

5. A rhinoplastic surgical kit according to claim 4, wherein said second connector element has said resilience.

6. A rhinoplastic surgical kit according to claim 4, wherein said resilience is due at least in part to said second connector element having one or more portions with a notch.

7. A rhinoplastic surgical kit according to claim 4, wherein said first connector element has said resilience.

8. A rhinoplastic surgical kit according to claim 7, wherein said resilience is due at least in part to said first connector element having portions spaced apart from each other which can be squeezed together to bring said first and second connector elements into said mechanical engagement and which are resilient against said second connector element to maintain said mechanical engagement.

9. A rhinoplastic surgical kit according to claim 4, wherein said first and second connector elements are at least approximately round.

10. A rhinoplastic surgical kit according to claim 4, wherein said first and second connector elements are at least approximately polygonal.

11. A rhinoplastic surgical kit comprising an augment, at least two implantable struts each having a first connector element, and at least one implantable element having a second connector element, said first and second connector elements being adapted to engage each other in such manner as to secure themselves together without use of screws, each said strut having at least one portion lying in a plane, and each said first connector element comprising material extending from its respective said strut in a direction that is perpendicular to said plane of that strut and defining a receptacle exhibiting a degree of resilience and at least a portion of which extends from that plane, and said second connector element comprising material having a shape and size to be received snappingly in either of said receptacles, and said first and second struts and said implantable element being provided in said kit with said first and said second connector elements not engaging each other.

* * * * *